United States Patent [19]

Erickson et al.

[11] E Patent Number: Re. 31,822

[45] Reissued Date of Patent: Feb. 5, 1985

[54] ABSORBENT FILMS AND LAMINATES

[75] Inventors: Robert E. Erickson, Midland; Richard M. Krajewski, St. Louis, both of Mich.

[73] Assignee: The Dow Chemical Company, Midland, Mich.

[21] Appl. No.: 132,928

[22] Filed: Mar. 24, 1980

Related U.S. Patent Documents

Reissue of:

[64] Patent No.: 4,117,184
Issued: Sep. 26, 1978
Appl. No.: 809,501
Filed: Jun. 23, 1977

U.S. Applications:

[63] Continuation-in-part of Ser. No. 693,260, Jun. 7, 1976, abandoned.

[51] Int. Cl.[3] ..... A61F 13/18

[52] U.S. Cl. ..... 128/156; 428/224; 264/45.1

[58] Field of Search ..... 128/287, 285, 284, 155, 128/156; 428/224; 264/45.1, 50

[56] References Cited

U.S. PATENT DOCUMENTS

| | | | |
|---|---|---|---|
| 3,081,181 | 3/1963 | Rutenberg et al. | 264/50 |
| 3,650,995 | 3/1972 | Erickson | 264/50 |
| 3,663,462 | 5/1972 | Arndt et al. | 264/50 |
| 3,669,103 | 6/1972 | Harper et al. | 128/156 |
| 3,670,731 | 6/1972 | Harmon | 128/156 |
| 3,686,024 | 8/1972 | Nankee et al. | 128/287 X |
| 3,887,408 | 6/1975 | Hoey | 156/78 |
| 3,926,891 | 12/1975 | Gross et al. | 260/29.6 |
| 3,954,721 | 5/1976 | Gross | 128/156 |
| 3,980,663 | 9/1976 | Gross | 128/156 |
| 4,000,028 | 12/1976 | Hoey | 156/246 |

*Primary Examiner*—Benjamin R. Padgett
*Assistant Examiner*—T. J. Wallen
*Attorney, Agent, or Firm*—B. G. Colley

[57] ABSTRACT

Water swellable aerated films and laminates, made from solutions of carboxylic polyelectrolytes, together with methods for their preparation, are disclosed. The films and laminates are cured and/or crosslinked with a polyfunctional or difunctional crosslinking agent that is reactive with carboxylate groups by heating and/or removing substantially all of the water and/or alcohol from the precursor composition. The solutions are mechanically aerated prior to the curing step.

The absorbent articles have a rapid water absorbency rate and are useful as components in diapers, tampons, dressings and the like.

32 Claims, 2 Drawing Figures

ABSORBENT FILMS AND LAMINATES

Matter enclosed in heavy brackets [ ] appears in the original patent but forms no part of this reissue specification; matter printed in italics indicates the additions made by reissue.

CROSS REFERENCE TO RELATED APPLICATIONS

This application is a continuation-in-part of Ser. No. 693,260 filed June 7, 1976, and now abandoned.

BACKGROUND OF THE INVENTION

This invention relates to water swellable absorbent aerated films or laminates made from crosslinked polyelectrolytes, and methods for their preparation.

It is known from U.S. Pat. Nos. 3,669,103 and 3,670,731 that crosslinked polymeric sorbents can be sandwiched between flexible supports to achieve disposable diapers or dressings.

The patent application by W. D. Burkholder, Ser. No. 565,880, filed Apr. 7, 1975, discloses methods of curing polyelectrolytes to make water swellable films wherein the curing or crosslinking agent is a polyamido-polyamine epichlorohydrin adduct. The patent to J. R. Gross, U.S. Pat. No. 3,980,663, discloses absorbent articles films, etc. and methods for their preparation wherein the crosslinking agents used are difunctional crosslinking agents which are reactive with carboxylate groups.

However, it has been found that the films prepared by Ser. No. 565,880 and U.S. Pat. No. 3,980,663 do not have the required rapid water absorbency rate so that water, urine, and other hydrophilic body fluids will be absorbed substantially within the time period required for practical use as in disposable diapers or pads.

SUMMARY OF THE INVENTION

It now has been discovered that films and laminates of lightly crosslinked carboxylic polyelectrolytes can be made wherein the polyelectrolyte formulation is aerated before it is crosslinked and this gives a rapid water absorbency rate.

The present invention is a water swellable aerated film which is characterized by being rapidly wetted and swelled by water and which comprises a lightly crosslinked carboxylic polyelectrolyte having a density ranging from about 0.3 to about 1.1 grams per cc and a water absorbency rate of not greater than 60 seconds. Preferably the film has a density of from 0.5 to about 0.9 grams per cc and the water absorbency rate is not greater than 55 seconds, and most advantageously is not greater than 50 seconds.

A further aspect of the present invention comprises a water swellable aerated laminate which comprises one or more layers of the above aerated film on substrates consisting of woven fabric, non-woven fiber mat, polymeric foam, polymer film, or paper.

The invention further comprises a method for making the above aerated films which comprises the steps of (1) mechanically aerating a solution so as to introduce greater than 8% by weight of air wherein said solution has about 10% to about 25% by weight of a solvent consisting of water, lower alcohols, or mixtures thereof wherein the solids comprise (a) about 75 to about 99.5% of a carboxylic polyelectrolyte, and (b) about 0.5 to about 5.0% of a polyfunctional or difunctional crosslinking agent that is reactive with carboxylate groups, (2) casting a wet film of said solution on a moving impervious support having a release surface, and (3) heating the film to a temperature range from about 30° C. to about 175° C. to crosslink and remove substantially all the solvent.

Still further, the invention comprises a method for making the above aerated film having a roughened surface which comprises the steps of (1) preparing a solution having about 10 to about 25% by weight solids and about 75 to about 90% by weight of a solvent consisting of water, lower alcohols, or mixtures thereof wherein the solids comprise (a) about 75 to about 99.5% of a carboxylic polyelectrolyte, and (b) about 0.5 to about 5.0% of a polyfunctional or difunctional crosslinking agent that is reactive with carboxylate groups, (2) casting a wet film of said solution on a moving impervious support having a release surface which support is heated to a temperature range from about 90° C. to about 175° C. to effect a partial crosslinking, (3) feeding said film after said partial cross-linking through a forced air zone whereby hot air at a temperature range from about 100° C. to about 200° C. is impinged upon the surface of the film.

In order to obtain very high production rates of the absorbent films, it may be desirable to replace part or nearly all of the water in the polyelectrolyte solution with a lower alcohol such as methanol or ethanol. This substitution results in lower solution viscosities at a given percent solids and promotes rapid drying.

The final products of the present invention are thus rapidly water swellable and are useful wherever aqueous solutions such as urine, blood, etc., need to be absorbed. Examples of the diverse utilities are catamenial tampons, diapers, paper towels, disposable door mats, disposable bath mats and disposable litter mats for household pets.

DETAILED DESCRIPTION

Figure 1:
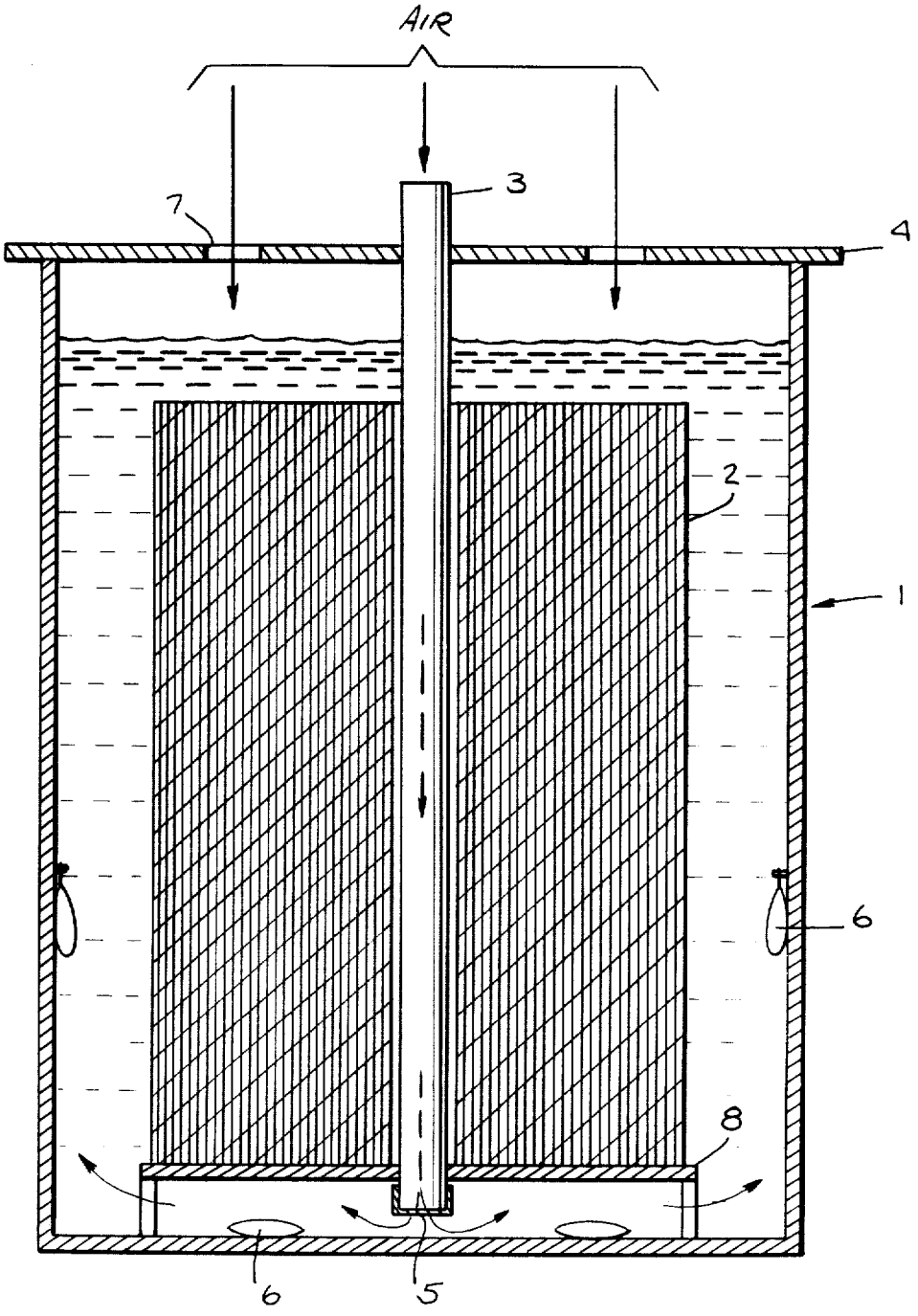
Figure 2:
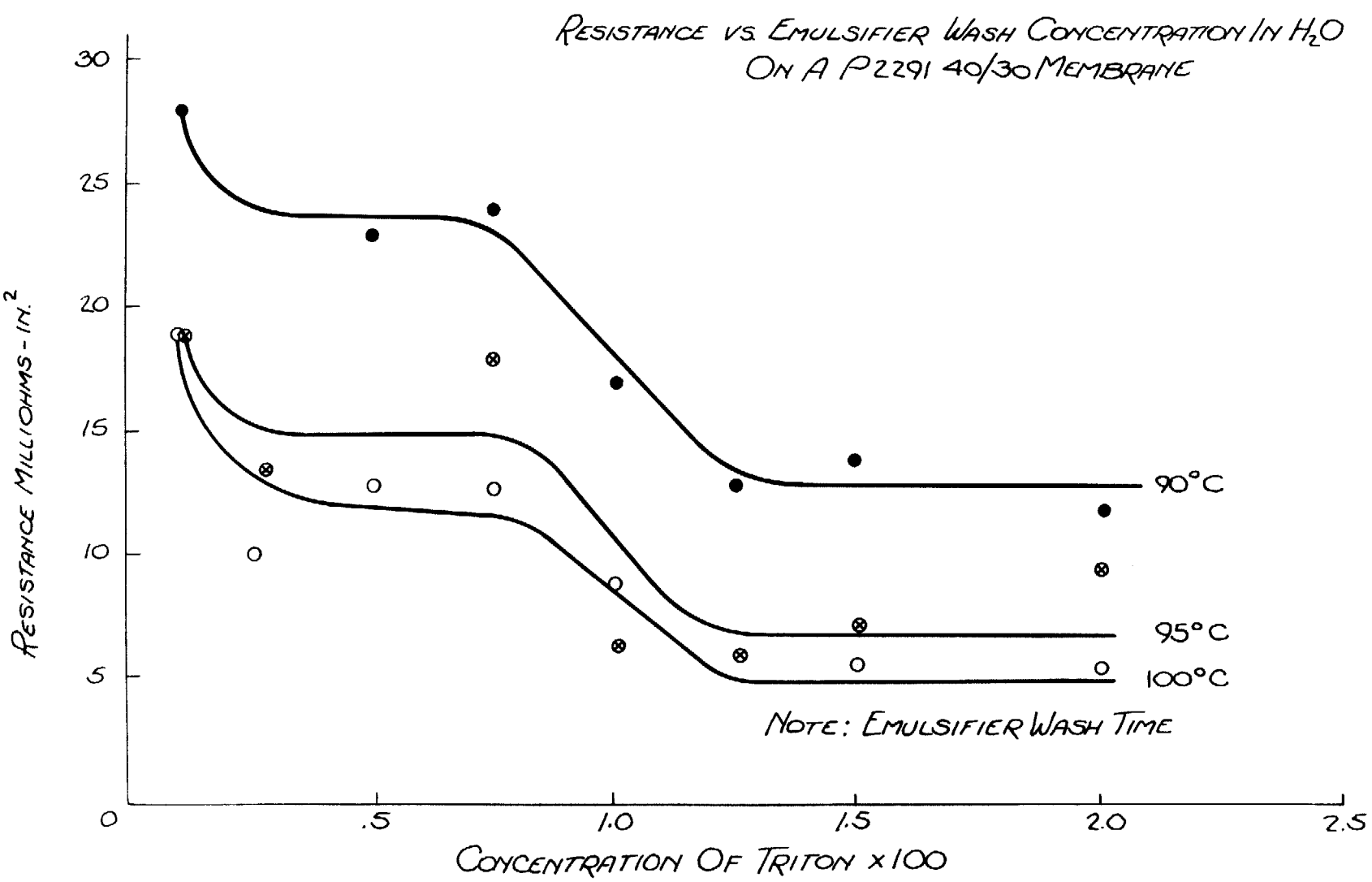

Polyelectrolytes useful in this invention must be essentially water soluble in the salt form. Examples of useful polyelectrolytes include ammonium or alkali metal salts of homopolymers of acrylic or methacrylic acid and copolymers with one or more ethylenically unsaturated comonomers.

Preferably the polyelectrolyte is a partially saponified polyacrylate polymer. The polymer before saponification is the result of reacting together a mixture of monomers which comprises (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid; and (3) 0 to 15 percent by weight of an omega hydroxyalkyl acrylate wherein the hydroxyalkyl groups has from 1 to 4 carbon atoms.

Examples of useful alkyl acrylates include methyl acrylate, ethyl acrylate, propyl acrylate and hexyl acrylate. Examples of useful alkyl methacrylates include butyl methacrylate, hexyl methacrylate, octyl methacrylate and decyl methacrylate. Examples of useful omega hydroxyalkyl acrylates include 2-hydroxyethyl acrylate, hydroxymethyl acrylate, 3-hydroxypropyl acrylate and 4-hydroxybutyl acrylate.

The olefinically unsaturated carboxylic acids useful in this invention are mono or polycarboxylic acids. Examples of monocarboxylic acids include acrylic acid, methacrylic acid, crotonic acid, and isocrotonic acid. Examples of polycarboxylic acids include maleic acid, fumaric acid, and itaconic acid.

The foregoing polyacrylates are then dissolved in an aqueous alkali metal hydroxide solution. The amount of hydroxide solution employed is sufficient to saponify some of the acrylate esters to alkali metal carboxylates and to neutralize the carboxylic groups of the polyacrylate to alkali metal carboxylates so that the saponified polyacrylate polymer has from 30 to 70 weight percent alkali metal carboxylates.

The partially saponified polyacrylate polymer is employed as a solution containing from 5 to 60 percent by weight of the polymer.

A list of applicable polymers which could be prepared from readily available monomers and converted into their salt form is as follows:

acrylic acid—acrylate copolymers
acrylic acid—acrylamide copolymers
acrylic acid—olefinic copolymers polyacrylic acid
acrylic acid—vinyl aromatic copolymers
acrylic acid—styrene sulfonic acid copolymers
acrylic acid—vinyl ether copolymers
acrylic acid—vinyl acetate copolymers
acrylic acid—vinyl alcohol copolymers
copolymers of methacrylic acid with all the above comonomers.

If desired, the foregoing polyelectrolytes can also be sulfonated by treatment with sulfur trioxide, chlorosulfonic acid or fuming sulfuric acid in an inert organic solvent.

Illustrative examples of the polyfunctional crosslinking agents useful in this invention are set forth in U.S. Pat. Nos. 2,926,154; 3,224,986; and 3,332,901. These polyfunctional crosslinking agents are generally known as polyamide-polyamine epichlorohydrin adducts. The disclosures of these references are incorporated herein by reference. Similar crosslinking agents are also commercially available from Hercules Incorporated as Kymene 557 and Polycup 172. The structure of these adducts has been discussed in an article by M. E. Corr et al. Journal of Applied Polymer Science vol. 17, pages 721–735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as crosslinking agents are monomeric amine-epihalohydrin adducts prepared by reacting at least two moles of an epihalohydrin with one mole of various monoamines, diamines and triamines at a temperature in the range from 0° to 90° C. for a time period of 0.5 to 8 hours. The reaction is carried out in a reaction media containing 20 to 90 percent water, lower alcohols such as methanol or ethanol, or in aqueous solutions of the lower alcohols. The amine-epihalohydrin adducts are used directly as made without separation or concentration. The preparation and use of amino-epihalohydrin adducts as crosslinking agents is further disclosed in the patent application by J. R. Gross, Ser. No. 796,627 filed May 13, 1977. This application is incorporated by reference herein.

Sulfonium zwitterions are known from U.S. Pat. Nos. 3,660,431, 3,749,737 and 3,749,738. The disclosures of these patents are incorporated herein by reference.

These crosslinking agents are used in an amount from about 0.5 to about 5.0% based on the weight of the polyelectrolyte used. This is generally sufficient to cause the polyelectrolyte to become lightly crosslinked.

In the preferred method of making water swellable films by the present invention, the above composition of the polyelectrolytes is mechanically aerated and spread on a heated roller of metal, plastic or other impervious substrate and dried to crosslink the polyelectrolyte and drive off the excess water and/or alcohol. The film is then stripped or peeled off the roller to recover the intact film for subsequent storage or use.

For the purposes of this invention, a film is defined as having a thickness of 0.1 to 10.0 mils and preferably from 1 to 3 mils.

It is sometimes desirable to add a small amount of a surfactant to the polyelectrolyte composition to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and the ethylene oxide derivatives of alkylated phenols and the like.

If desired, the water-swellable film prepared as above can be used per se as the inner absorbent layer in baby or adult diapers.

The absorbency of the crosslinked films (grams solution gelled per gram of polyelectrolyte) is determined in the following manner using synthetic urine (1.6 weight percent sodium chloride solution). The absorbency of the films is much higher using deionized water.

A 0.5 gram samples of a crosslinked polyelectrolyte is weighed into a 250 ml. beaker, a 1.6 weight percent sodium chloride solution (150 ml.) is poured into the beaker and allowed to soak for about 30 minutes at room temperature, with occasional stirring. The swelled polyelectrolyte is then collected by filtration and the gel capacity is reported as grams of solution gelled per gram of polymer salt.

For the purpose of this invention, a moisture or water absorbent or water swellable polyelectrolyte is defined as one which adsorbs greater than about 15 times its weight of synthetic or natural urine. Preferably the absorbency should be in the range from about 20–40 gram of urine per gram of polyelectrolyte or in the range of 90–250 grams of deionized water per gram of polyelectrolyte. The level of crosslinking agent used is a variable factor which is dependent upon the particular polyelectrolyte used and the molecular weight of the polyelectrolyte. In general, the amount used varies from the 0.5 to 5.0 percent based on the weight of the polyelectrolyte. However, this range is varied for each polyelectrolyte in order to adjust the absorbency of the final crosslinked gel.

The water swellable films of this invention may be combined into laminates with wicking or non-wicking substrates. Examples of wicking substrates include woven fabrics, non-woven fiber mats, polymeric foams, tissue paper, crepe paper and toweling. Examples of non-wicking substrates include polymer films such as polyethylene, polypropylene and polystyrene; and hard surface papers such as Kraft and writing paper.

EXAMPLES 1 THROUGH 5 AND COMPARATIVE RUNS A THROUGH E

Polyelectrolyte A employed in Examples 1 through 5 and Comparative Runs A through E was prepared from a polymeric latex that contained 83 mole percent ethyl acrylate and 17 mole percent methacrylic acid. The latex was saponified with sodium hydroxide to the extent that the polymer of polyelectrolyte A contained 50 mole percent ethyl acrylate, 33 mole percent sodium acrylate and 17 mole percent sodium methacrylate. Polyelectrolyte A contains 25.8 weight percent solids.

Crosslinking Agent B employed in Examples 1 and 2 and Comparative Runs A and B was a liquid adduct of epichlorohydrin and a polyamide-polyamine. Crosslinking agent B contains 4.2 weight percent solids, 4.3 weight percent nitrogen and has a pH between 4.6 and 4.9.

Crosslinking Agent C employed in Examples 3 and Comparative Run C was a methanol solution containing 5 weight percent of an polyglycol diepoxide having an EEW of 181.

Crosslinking Agent D employed in Example 4 and Comparative Run D was a 5 percent by weight solution of an epichlorohydrin adduct of piperazine prepared by reacting 2 moles of epichlorohydrin with one mole of piperazine.

Crosslinking Agent E employed in Example 5 and Comparative Run E was a 24 weight percent solution of a cyclic sulfonium zwitterion of bisphenol A in water. The cyclic sulfonium zwitterion was prepared by reacting 2 moles of tetrahydrothiophene with one mole of bisphenol A.

Surfactant F employed in Examples 1, 3, 4, and 5 and Comparative Runs A, C, D, and E is polyoxyethylene sorbitan monolaurate.

In Example 1, Polyelectrolyte A, Crosslinking Agent B, Surfactant D, and additional water were mixed in a high speed blender for one minute. During the mixing air was entrapped in the formulation increasing the volume of the formulation by about 50 percent. The mixed formulation was cast on a commercial release coated paper employing a 15 mil (0.38 mm) gap casting bar. The wet film was dried in an air circulating oven at 250° F. (121° C.) for 20 minutes. The film was allowed to condition at 50% relative humidity for 1 hour and was then removed from the release coated paper.

In Comparative Run A, the same formulation was prepared but it was only mixed in the normal manner of paddle mixing with a minimum amount of air entrapped in the mixed formulation. The mixed formulation was cast on a commercial release coated paper with a 20 mil (0.51 mm) gap casting bar.

In Example 2 and Comparative Run B, the same procedures were followed as in Example 1 and Comparative Run A, respectively, except that the formulations did not contain Surfactant D.

In Example 3 and Comparative Run C, the same procedures were followed as in Example 1 and Comparative Run A, respectively, except that Crosslinking Agent C was employed in place of Crosslinking Agent B, and the films were dried at 347° F. (175° C.).

In Example 4 and Comparative Run D, the same procedures were followed as in Example 1 and Comparative Run A, respectively, except that Crosslinking Agent D was employed in place of Crosslinking Agent B and the mixed formulation was cast on a glass plate that contained a release coating. The glass plate was heated to 250° F. (121° C.) before the formulation was cast. The wet film was dried in an air circulating oven at 250° F. (121° C.) for 20 minutes.

In Example 5 and Comparative Run E, the same procedures were followed as in Example 4 and Comparative Run D, respectively, except that Crosslinking Agent E was employed in place of Crosslinking Agent D and the films were dried at 250° F. (121° C.) for 30 minutes.

Water absorbency rates were determined for all films from Examples 1 through 5 and Comparative Runs A through E. The water absorbency rate was measured by placing a 1 by 3 inch (2.5 by 7.6 cm) sample of a water swellable film on the 4.5 by 8 inch (11.4 by 20.3 cm) glass plate base of a stereoscopic microscope. One drop of deionized water was gently placed on the surface of the film and observed through the microscope at 20X magnification. The number of seconds required for the drop of water to be completely absorbed by the film was the absorbency rate. Complete absorption means all motion and/or swelling of the film ceases.

The formulations and properties of the films produced in Examples 1 through 5 and Comparative Runs A through E are shown in Table 1.

TABLE I

| Formulation in Parts | Ex. 1 | Comparative Run A | Ex. 2 | Comparative Run B | Ex. 3 | Comparative Run C |
|---|---|---|---|---|---|---|
| Polyelectrolyte A | 364.34 | 364.34 | 364.34 | 364.34 | 365.8 | 365.8 |
| Crosslinking Agent B | 24.04 | 24.04 | 24.04 | 24.04 | — | — |
| Crosslinking Agent C | — | — | — | — | 12.5 | 12.5 |
| Crosslinking Agent D | — | — | — | — | — | — |
| Crosslinking Agent E | — | — | — | — | — | — |
| Surfactant F | 5.0 | 5.0 | — | — | 5.0 | 5.0 |
| Water | 106.62 | 106.62 | 106.62 | 106.62 | 116.7 | 116.7 |
| Properties | | | | | | |
| Film Thickness, mils (mm) | 3.2 | 2.7 | 3.2 | 2.7 | 3.2 | 3.0 |
| Film Density g/cc | 0.6 | 1.2 | 0.6 | 1.2 | 0.75 | 1.16 |
| Absorbency Rate, Seconds | 35 | 65 | 50 | 75 | 45 | 90 |

| Formulation in Parts | Ex. 4 | Comparative Run D | Ex. 5 | Comparative Run E |
|---|---|---|---|---|
| Polyelectrolyte A | 364.34 | 364.34 | 364.34 | 364.34 |
| Crosslinking Agent B | — | — | — | — |
| Crosslinking Agent C | — | — | — | — |
| Crosslinking Agent D | 20.0 | 20.0 | — | — |
| Crosslinking Agent E | — | — | 4.17 | 4.17 |
| Surfactant F | 5.0 | 5.0 | 5.0 | 5.0 |

TABLE I-continued

| | | | | |
|---|---|---|---|---|
| Water | 110.66 | 110.66 | 126.49 | 126.49 |
| Properties | | | | |
| Film Thickness, mils (mm) | 3.1 | 3.0 | 3.0 | 2.6 |
| Film Density g/cc | 0.6 | 1.15 | 0.7 | 1.18 |
| Absorbency Rate, Seconds | 40 | 70 | 44 | 75 |

The mixing of the formulation in Examples 1 through 5 in a blender entraps air in the formulation. When the formulation was dried to a film, the film was observed to have small air bubbles in the film and craters from opened air bubbles on the surface of the film. The examples of aerated films show markedly improved absorbency rates over the Comparative Runs of unaerated films.

EXAMPLES 6, 7, 8, 9, AND 10

In Example 6, the formulation of Example 1 was mixed in a blender by first adding Polyelectrolyte A, Surfactant D and the water and then slowly adding Crosslinking Agent B. The mixed formulation was placed in a paint pressure pot and pressure fed to a metering pipe in front of a casting bar on the top surface of a heated steel drum coated with polytetrafluoroethylene at a rate sufficient to minimize puddle formation in front of the casting bar.

The steel drum was 12 inches (30.5 cm) in diameter and 21 inches (53.3 cm) long. The drum was heated to 215° F. (102° C.) and rotated at a surface speed of 2.2 feet per minute (0.67 meters per minute). The cast wet film had a thickness of 15 mils (0.38 mm). The film was allowed to dry on the drum for 1.5 minutes and then removed from the surface of the drum dryer. The film, containing between 8 and 10 weight percent moisture, was wound on a cardboard core and packaged in a polyethylene bag to retain the moisture in the film and thus maintain the flexibility of the film.

In Example 7, the procedure of Example 6 was repeated with the addition that after the film had rotated 6 inches (15.2 cm), it then passed under a forced hot air blower where the air at about 400° F. (204° C.) impinged directly on the surface of the wet film. This additional step facilitated more rapid drying of the film and caused a surface blistering or roughening which resulted in a fast absorbency rate.

In Example 8, the procedure of Example 6 was repeated with the additional step of having a crimped paper tissue, 25 pounds (11.3 kilograms) per reem, fed onto the outside of the wet film within the first 6 inches (15.2 cm) of drum travel. Two hot air blowers held the tissue against the film surface during drying. The laminate was removed from the drum and wound on a cardboard core.

In Example 9, the procedure of Example 8 was repeated with the variation that the film was dried to about 8 weight percent moisture. Next the surface of the film was moistened with a water mist. Then the tissue was pressed against the moistened surface of the film. The film and tissue were passed under a pressure roll (about 1.2 psi) so that the tissue was lightly bonded to the surface of the film. The laminate was wound on a cardboard core.

In Example 10, the same procedure of Example 6 was repeated with the variation that the formulation was cast by reverse roll on a 46 inch (117 cm) wide stainless steel endless belt coated with a silicone release agent and traveled at a rate of 20 feet per minute (6 meters per minute). The endless belt containing the wet film was passed through a hot air oven at 200° F. (93° C.) where the film was cured and dried in a residence time of 1.85 minutes. After leaving the oven, the film was removed from the endless belt, wound on a cardboard core and stored.

The thicknesses, densities and absorbency rates for the films of Examples 6, 7, 8, 9, and 10 are reported in Table II.

TABLE II

| Properties | Ex. 6 | Ex. 7 | Ex. 8 | Ex. 9 | Ex. 10 |
|---|---|---|---|---|---|
| Film Thickness, mils (mm) | 3.0 | 2.8 | 3.2 | 3.5 | 1.6 |
| Film Density, g/cc | 0.8 | 0.8 | 0.9 | 0.8 | 0.86 |
| Absorbency Rate, Seconds | 35 | 35 | 50 | 55 | 35 |

We claim:

1. A water swellable aerated film which is characterized by being rapidly wetted and swelled by water which comprises a lightly crosslinked alkali metal carboxylic polyelectrolyte having a density ranging from about 1.1 grams per cubic centimeter to about 0.3 grams per cc and a water absorbency rate of not greater than 60 seconds.

2. The film as set forth in claim 1 wherein the polyelectrolyte is crosslinked with a polyfunctional or difunctional crosslinking agent that is reactive with carboxylate groups.

3. The film as set forth in claim 2 wherein the polyfunctional crosslinking agent is a polyamidepolyimine epichlorohydrin adduct.

4. The film as set forth in claim 2 wherein the difunctional crosslinking agent is a diglycidyl ether.

5. The film as set forth in claim 3 wherein the aerated film has a roughened surface.

6. The film as set forth in claim 2 wherein the aerated film has a roughened surface.

7. An aerated film as set forth in claim 1 wherein the polyelectrolyte consists of an alkali metal salt of a polyacrylate.

8. An aerated film as set forth in claim 1 wherein the polyelectrolyte consists of a terpolymer of ethyl acrylate, sodium acrylate, and sodium methacrylate with 50 mole percent being ethyl acrylate.

9. A water swellable aerated laminate which comprises one or more layers of the film of claim 1 on wicking substrates consisting of woven fabrics, non-woven fiber mats, or polymeric foams.

10. A water swellable aerated laminate which comprises one or more layers of the film of claim 1 on non-wicking substrates consisting of polymer films or papers.

11. A water swellable aerated laminate as set forth in claim 9 wherein the film consists of a terpolymer of ethyl acrylate, sodium acrylate, and sodium methacrylate with 50 mole percent being ethyl acrylate.

12. A water swellable aerated laminate as set forth in claim 10 wherein the film consists of an alkali metal salt of a polyacrylate.

13. A water swellable aerated laminate as set forth in claim 10 wherein the film consists of a terpolymer of ethyl acrylate, sodium acrylate, and sodium methacrylate with 50 mole percent being ethyl acrylate.

14. A method for making the aerated film of claim 1 which comprises the steps of (1) mechanically aerating a solution so as to introduce greater than 8% by weight of air wherein said solution has about 10 to about 25% by weight solids and about 75 to about 90% by weight of a solvent consisting of water, lower alcohols, or mixtures thereof wherein the solids comprise
   (a) about 75 to about 99.5% of an alkali metal carboxylic polyelectrolyte, and
   (b) about 0.5 to about 5.0% of a polyfunctional or difunctional crosslinking agent that is reactive with carboxylate groups,
(2) casting a wet film of said solution on a moving impervious support having a release surface, and
(3) heating the film to a temperature range from about 30° C. to about 175° C. to crosslink and remove substantially all the solvent.

15. A method for making the aerated film of claim 1 having a roughened surface which comprises the steps of (1) mechanically aerating a solution so as to introduce greater than 8% by weight of air wherein said solution has about 10 to about 25% by weight solids and about 75 to about 90% by weight of a solvent consisting of water, lower alcohols, or mixtures thereof wherein the solids comprise
   (a) about 75 to about 99.5% of an alkali metal carboxylic polyelectrolyte, and
   (b) about 0.5 to about 5.0% of a polyfunctional or difunctional crosslinking agent that is reactive with carboxylate groups,
(2) casting a wet film of said solution on a moving impervious support having a release surface which support is heated to a temperature range from about 90° C. to about 175° C., to effect a partial crosslinking,
(3) feeding said film after said partial crosslinking through a forced air zone whereby hot air at a temperature range from about 100° C. to about 200° C. is impinged upon the surface of the film.

16. A method as set forth in claim 14 wherein the polyelectrolyte consists of an alkali metal salt of a polyacrylate.

17. A method as set forth in claim 14 wherein the polyelectrolyte consists of a terpolymer of ethyl acrylate, sodium acrylate, and sodium methacrylate with 50 mole percent being ethyl acrylate.

18. A method as set forth in claim 15 wherein the polyelectrolyte consists of an alkali metal salt of a polyacrylate.

19. A method as set forth in claim 15 wherein the polyelectrolyte consists of a terpolymer of ethyl acrylate sodium acrylate, and sodium methacrylate with 50 mole percent being ethyl acrylate.

20. The product produced by the method of claim 14.

21. The product produced by the method of claim 15.

22. The product produced by the method of claim 16.

23. The product produced by the method of claim 17.

24. The product produced by the method of claim 18.

25. The product produced by the method of claim 19.

*26. The method of making a disposable liquid absorbent pad for use as a diaper, sanitary napkin and the like comprising the steps of:*

*forming a film of polymeric material capable of forming a gel upon application of liquid thereto providing a crinkled absorbent sheet having apex portions for receiving said film there across; and*

*producing a controlled amount of gel on said film forming a limited bond with said sheet at the apex portions facilitating wicking of liquid applied to the pad thus formed through voids between apex portions of said crinkled absorbent sheet.*

*27. The method of claim 26, including spraying a limited amount of liquid for producing said controlled amount of gel on said film.*

*28. The method of making a water swellable laminate for use as a diaper, sanitary napkin and the like comprising the steps of:*

*forming a film of polymeric material capable of forming a gel upon application of liquid thereto;*

*providing a crinkled absorbent sheet having apex portions for receiving said film there across; and*

*producing a controlled amount of gel on said film forming a limited bond with said sheet at the apex portions facilitating wicking of liquid applied to said laminate thus formed through voids between apex portions of said crinkled absorbent sheet.*

*29. The method of claim 28 including spraying a limited amount of liquid for producing said controlled amount of gel on said film.*

*30. The method of claim 28 including spraying a limited amount of water for producing said controlled amount of gel on said film.*

*31. The method of making a water swellable laminate for use as a diaper, sanitary napkin and the like comprising the steps of:*

*forming a water based film of crosslinkable polymeric material;*

*drying said film to cause the crosslinking of said polymeric material;*

*providing a crinkled absorbent sheet having apex portions for receiving said film there across; and*

*producing a controlled amount of adhesive gel on said film forming a limited bond with said sheet at the apex portions facilitating wicking of liquid applied to said laminate thus formed through voids between apex portions of said crinkled absorbent sheet.*

*32. The method of claim 31 including spraying a limited amount of water for producing said controlled amount of adhesive gel on said film.*

* * * * *

UNITED STATES PATENT AND TRADEMARK OFFICE

CERTIFICATE OF CORRECTION

PATENT NO. : RE 31822

DATED : February 5, 1985

INVENTOR(S) : Robert E. Erickson et al

It is certified that error appears in the above-identified patent and that said Letters Patent is hereby corrected as shown below:

Title page: after "32 claims" insert --No Drawings--.

Please cancel sheet 1 of 2 and sheet 2 of 2.

Col. 5, line 30; "Examples" should read --Example--.

Signed and Sealed this

*Thirtieth* Day of *July 1985*

[SEAL]

*Attest:*

DONALD J. QUIGG

*Attesting Officer*

*Acting Commissioner of Patents and Trademarks*